United States Patent [19]

Behar et al.

[11] Patent Number: 4,710,354
[45] Date of Patent: Dec. 1, 1987

[54] DEVICE FOR HEATING OF SOLID OR LIQUID SAMPLES IN SMALL QUANTITIES

[75] Inventors: Françoise Behar, Paris; Jeannine Roucache, Le Chesnay; Jean Auger, Dourdan; Luc Boudet, Chelles, all of France

[73] Assignee: Institut Francais du Petrole, Rueil-Malmaison, France

[21] Appl. No.: 746,093

[22] Filed: Jun. 18, 1985

[30] Foreign Application Priority Data

Jun. 18, 1984 [FR] France ................. 84 09622

[51] Int. Cl.⁴ ........................................ G01N 31/12
[52] U.S. Cl. ........................ 422/80; 422/78; 422/199; 422/202; 422/241; 436/157
[58] Field of Search ...................... 422/78–80, 422/199, 202, 241; 436/155, 157; 219/300, 390; 373/137, 155

[56] References Cited

U.S. PATENT DOCUMENTS

| 1,986,196 | 1/1935 | Grosse | 422/241 |
| 2,382,301 | 8/1945 | Dreher | 422/78 |
| 3,494,743 | 2/1970 | Baughman et al. | 422/202 |
| 3,847,554 | 11/1974 | Su | 422/80 |

FOREIGN PATENT DOCUMENTS

| 2938343 | 4/1980 | Fed. Rep. of Germany | 422/78 |
| 2029014 | 3/1980 | United Kingdom | 436/157 |
| 763791 | 9/1980 | U.S.S.R. | 422/78 |

Primary Examiner—David L. Lacey
Attorney, Agent, or Firm—Antonelli, Terry & Wands

[57] ABSTRACT

A device useful for heating of samples taken in small amounts, comprising a sample holding rod engaging in a tubular liner while leaving a reduced dead or wasted space. The rod has an elongate cavity opening at its upper part and receiving the sample which is in contact with a vector gas. The sample holding rod has two positions one of which places the sample in a moderate temperature zone and the other of which places the sample in a heating zone.

9 Claims, 7 Drawing Figures

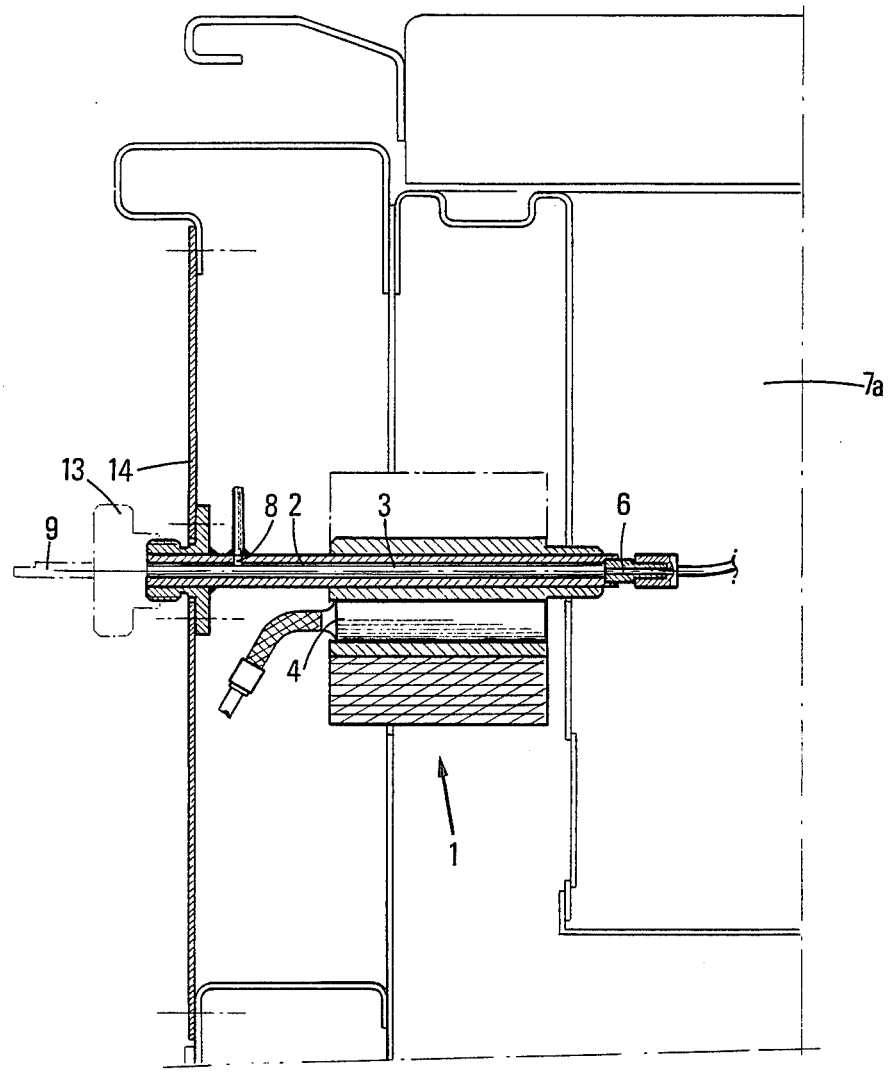

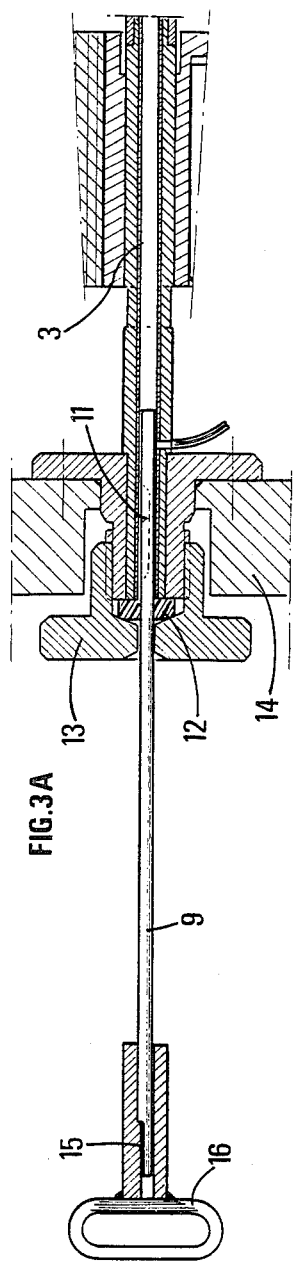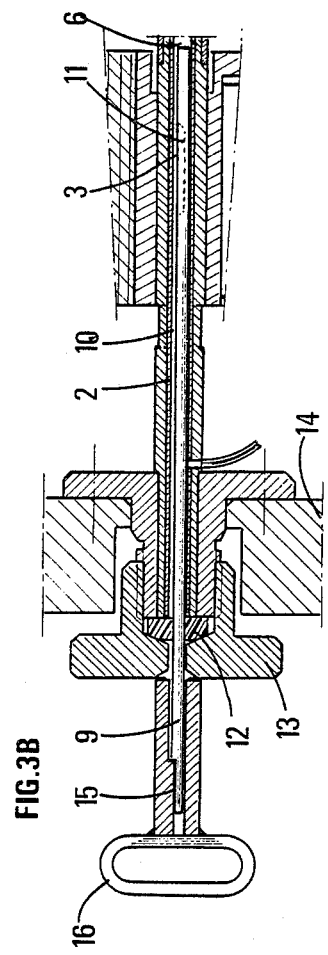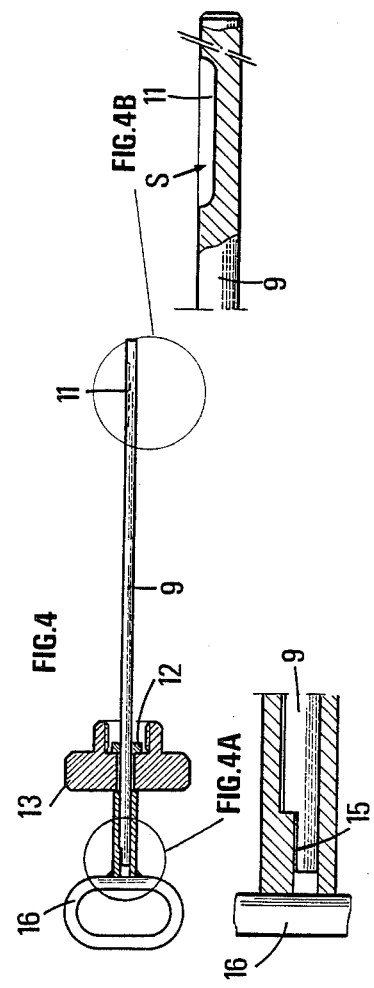

4,710,354

DEVICE FOR HEATING OF SOLID OR LIQUID SAMPLES IN SMALL QUANTITIES

BACKGROUND OF THE INVENTION

1. Field of the Invention

The present invention results from the work carried out at l'Institut Francais du Pétrole by Mesdames Francoise BEHAR and Jeannine ROUCACHE and at the DELSI Instruments firm by Messrs. Jean AUGER and Luc BOUDET.

This invention relates to a device usable for heating, and more particularly for the pyrolysis, of solid or liquid samples taken in small amounts.

The device of the invention is particularly suitable for carrying out the follow-up pyrolysis of the chromatographic analysis of pure organic materials (asphaltene kerogen, coal), or materials dispersed in a mineral matrix (recent sediments, source rocks), for example for establishing a relationship between the composition of the hydrocarbon fraction of a crude oil and its asphaltene pyrolysat, for establishing a correlation between the kerogen pyrolysats and the asphaltenes extracted from the same source rock, or else for knowing the modification of these pyrolysats with the geological evolution (depending on the depth in the same formation); these techniques being possibly used for effecting correlations between the crude oil and the source rock and correlations between crude oils.

The applications given above are however given solely by way of examples and must not therefore be considered as limiting the field of application of the device of the invention.

2. Description of the Prior Art

Devices are already known usable for the prolysis of samples taken in small amounts, these devices comprising a tubular liner inside which is defined a zone for heating the sample, heating means and means for measuring the temperature in said zone, a sample holder adapted to be introduced into the tubular liner as far as the heating zone. The tubular liner has an effluent outlet orifice which is connected to measurement and analysis apparatus. These devices comprise an orifice for introducing a vector gas for displacing these effluents, the orifices being situated on each side of said heating zone.

The sample holder is associated with a rod which is engaged in the tubular liner.

The main disadvantage of some of these prior devices is that the sample subjected to pyrolysis is situated in a confined space. This confined space is formed for example by a crucible having a cover, which does not allow complete scavenging of the sample by the vector gas.

Another disadvantage of the prior devices is that they have a relatively large useless volume between the pyrolysis oven and the trap where the pyrolysis products are retained or the measuring or/and analysis apparatus to which the oven is connected.

SUMMARY OF THE INVENTION

These disadvantages are overcome according to the invention with a device of the above mentioned type in which there exists between the rod and the liner a reduced annular space for the flow of the vector gas, the rod having an elongate cavity opening in its side wall into the annular space, the cavity being of small volume and adapted to receive the sample. Means for sealing and positioning the cavity in the tubular liner is fitted to said rod at one end of the tubular liner.

The tubular liner and the sample holding rod will be preferably disposed in a substantially horizontal direction, the cavity receiving the sample being placed so as to open upwardly.

In a particularly advantageous embodiment, the sealing and positioning means comprise a compressible ring in which the rod may slide, this ring cooperating with a closure member which is lockable, for example by threading or screwing, to the end of the tubular liner, ensuring simultaneously by compression of the ring sealing between the rod and the liner and immobilization of the sample in a position chosen beforehand inside the tubular liner.

The rod will be preferably movable between a first position in which the cavity containing the sample is situated in a moderate temperature zone of the tubular liner and a second position in which the cavity is situated in the heating zone.

Cooling means, such as a heat radiator, will be advantageously disposed at the level of the moderate temperature zone of the tubular liner.

The wall of the bore of the tubular liner, as well as that of the rod will be formed from a material chemically inert with respect to the pyrolysis effluents.

In a particularly preferred embodiment, the tubular liner has a bore whose internal wall is made from gold, the rod being also made from gold.

The rod may advantageously comprise means for locating the position of the cavity receiving the sample along and about the axis of the tubular liner when the rod is engaged in the liner.

BRIEF DESCRIPTION OF THE DRAWINGS

Embodiments of the devices in accordance with the invention are illustrated by the accompanying drawings in which:

FIG. 2 shows another embodiment for handling samples of reduced size, e.g. a micropyrolizer;

FIGS. 3A and 3B are schematical sections showing, respectively, the sample holding rod in a first position in which the sample is placed in a "cold" zone and in a second position where the sample is situated in the heating zone;

FIG. 4 shows the sample holding rod equipped with sealing and positioning means as well as its handling key; and FIGS. 4A and 4B are detail views on a larger scale of the ends of the sample holding rod.

DESCRIPTION OF THE PREFERRED EMBODIMENTS

Figure 1:
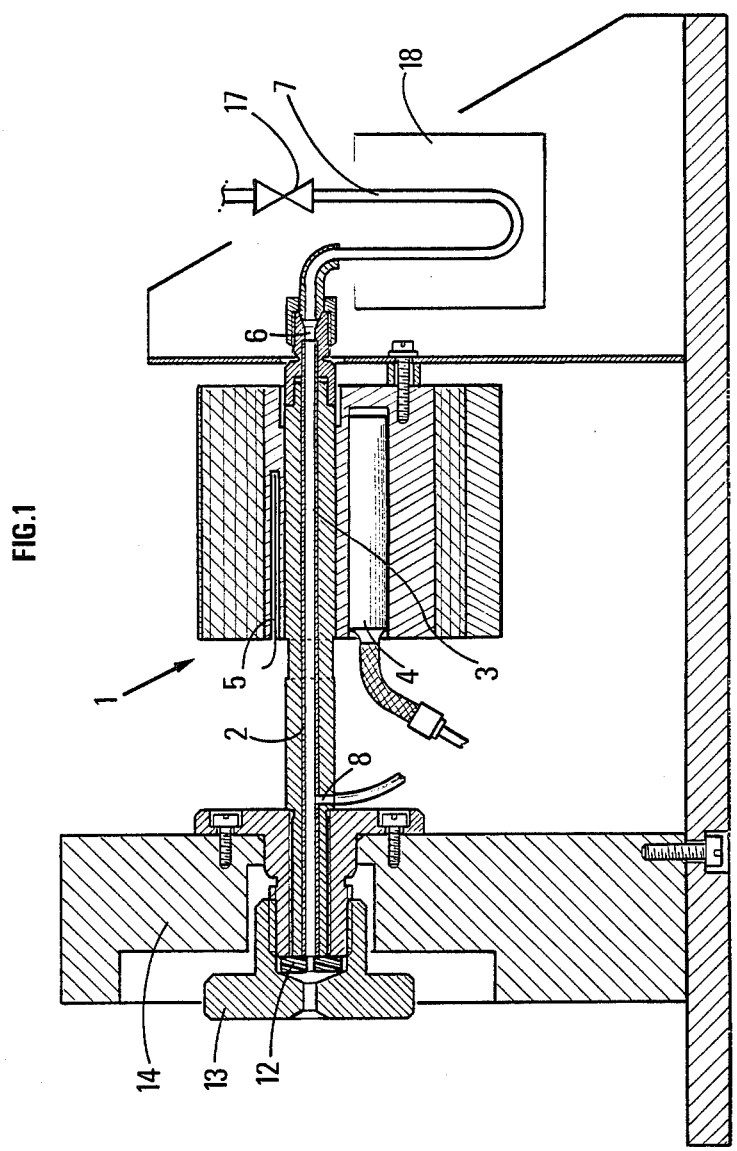
FIG. 1 shows a general view of a first embodiment of this device.

In the different figures, where the same numerical references have been used for designating the same parts, the reference 1 designates, as a whole, a tubular oven formed for example from Monel alloy and with a bore that has a wall formed by an internal tubular liner 2 inside which is defined a zone 3 for heating the sample.

Reference 4 designates means for heating the oven such as an electric resistance and reference 5 means for measuring the temperature in the heating zone 3 (thermocouple).

The tubular liner 2 has an effluent outlet orifice 6 which is connected to one or more traps 7 (FIG. 1)

or/and to measurement and analysis apparatus 7a, such as a gas phase chromatography apparatus (FIG. 2), and an orifice 8 for introducing a vector gas (argon for example) for driving along these effluents.

Apparatus 7a may also, for example, be formed by a flame ionization detector.

Orifices 6 and 8 are situated on each side of the heating zone 3.

The sample holder is formed essentially by a rod 9 which is engaged in the tubular liner 2 while leaving a reduced annular space 10 for vector gas flow.

The sample holder rod 9 has an elongate cavity 11 of small volume, or furrow, opening in the side wall of the rod. In the example illustrated, this cavity is of a very elongate shape adapted for receiving sample S in a layer of very small thickness. With the oven 1 disposed substantially horizontally, rod 9 is disposed in liner 2 so that cavity 11 receiving the sample opens upwardly. This arrangement reduces as much as possible the wasted volume inside the tubular oven 1.

The device also comprises means for sealing and positioning the cavity 11 in the tubular liner 2, these means being fitted to one end of liner 2.

In the embodiment illustrated, the means comprises a compressible ring 12 in which rod 9 may slide, this ring cooperating with a member 13 for closing the oven which is lockable, for example by screwing, at the end of the oven while ensuring simultaneously, by compression of ring 12, a seal between rod 9 and liner 2 as well as immobilization that cavity 11, so that sample S is in a position chosen beforehand inside the tubular liner 2.

The above described device has the advantage of comprising no valve or flow dividing member in the path of the pyrolysis effluents.

The sample holding rod 9 is movable between a first position (FIG. 3A) in which the cavity 11 containing sample S is situated in a moderate temperature zone of the tubular liner 2 and a second position (FIG. 3B) in which a cavity 11 is situated in said heating zone 3.

Cooling means, formed by a heat radiator 14, are situated at the level of the moderate temperature zone, or "cold zone" of the tubular liner.

In a particularly preferred embodiment, the rod as well as the liner 2, or at least its internal wall is made from gold.

The embodiment in which the liner 2 and rod 9 are made from gold has the following advantages:

(a) no risk of chemical reaction between the rod and the sample, cavity 11 may be readily cleaned after each test, for example by means of an oxygen jet at 550° C. which burns the residues;

(b) reduction of the temperature gradient all along the liner 2 (for example when the heating zone is at 550° C., the temperature at the outlet of the oven is about 400° C., whereas it would only be about 300° C. if liner 2 were made from Monel alloy like the tubular oven 1).

This arrangement also avoids risks of condensation of the heavy products of the pyrolysis effluents between the heating zone 3 and the trap 7 or the measuring and detection apparatus 7a connected to the outlet of the oven. This advantage is essential in the example for the pyrolysis of asphaltenes and kerogens, where the heavy products may represent up to 70% of the effluents.

With the adopted construction (liner 2 made from gold), these heavy products reach trap 7 or the measuring and analysis apparatus 7a.

(c) ease of introduction of the sample holding rod 9 in liner 2.

Experience shows in fact that because of the small annular clearance between these elements, a stainless steel rod may, by twisting, be jammed in liner 2 and it may not be possible to reintroduce it into the liner; whereas a rod made from gold, a malleable metal, is always readily engaged and withdrawn.

Means for locating the position of the cavity 11 inside liner 2 and about the axis of the rod when rod 9 is engaged in the liner comprise a flat portion 15 formed on rod 9. This flat portion allows rod 9 to be positioned in particular so that cavity 11 containing sample S is open upwardly.

The position of flat portion 15 is determined so that it remains outside liner 2 when rod 9 is engaged therein, cavity 11 being positioned in the heating zone 3.

A handling means or key 16 can be fitted to the end of rod 9 opposite the one engaged in liner 2 (FIGS. 4 and 4A). This key is adapted for limiting the engagement of rod 9 in liner 2 by coming into abutment against the closure member 13 in the position illustrated in FIG. 3B.

In order to limit as much as possible the wasted volume in the oven during pyrolysis, the length of rod 9 is advantageously chosen so that in its engagement position illustrated in FIG. 3B, the end of the rod engaged in liner 2 substantially reaches the effluent outlet orifice 6.

Examples will be given hereafter of different modes of operation of the device which has just been described.

The sample holding rod 9 is weighed before and after sample S has been placed in cavity 11 (FIG. 4B).

The end of rod 9 close to cavity 11 is introduced into the oven, the other end of the rod being engaged in the compressible ring 12 (made for example from silicon) disposed in the closure member 13 (FIG. 4) which is screwed on the end of the oven 1 situated at the level of the radiator 14.

With ring 12 situated in this "cold" zone of the oven there is no risk of releasing polluting products during the rise in temperature of the oven.

As long as member 13 is not threaded tightly, rod 9 may slide in ring 12 and cavity 11 may be placed in the "cold" zone of the oven opposite the radiator. 14.

In the embodiment of the invention illustrated in FIG. 1, a sample amount will be used, for example between 5 and 100 milligrammes and in the embodiment illustrated in FIG. 2, or micropyrolyzer, a sample amount between 25 and 200 microgrammes will be used.

The vector gas (argon for example) is fed in just behind the heat radiator 14, as close as possible to the inlet of the oven, which provides scavenging eliminating the residual air contained in the oven.

The output of the oven may be connected directly to a gas phase chromatography apparatus, but in the embodiment illustrated this outlet is connected to a trap 7 of known type whose outlet orifice is equipped with a valve 17 placed in an open position during this scavenging step, which allows the vector gas to escape.

When this step is finished, either rod 9 is pushed into the cold oven until the sample is positioned in the heating zone 3 (position located by the flat portion 15), then the temperature rise of the oven is programmed, or the oven is preheated before pushing in the rod. In this latter case, the sample is brought substantially immediately up to temperature (semi-flash) because of the heat conductivity of gold.

In both cases, locking of the closure member 13 provides both sealing and immobilization of sample S in the heating zone 3.

Before any pyrolysis, a check is made that the sample contains no vaporizable fraction by subjecting it to preheating before beginning the programming that brings the temperature of the sample S up to 550° C., for example.

Alternately, after carrying out such preheating, the rod is withdrawn for replacing the sample in the cold zone (after having slightly unscrewed the closure member 13).

Then the oven is heated up to 550° C., for example, before replacing sample S in the heating zone 3 of the oven.

The outlet valve of trap 7 is closed during the heating operation and trap 7 is surrounded by a container 18 containing the liquid nitrogen.

Since the argon leaving the oven liquifies in contact with the liquid nitrogen, the pyrolysis products are condensed with the argon in the trap.

Such a result could not be obtained if the vector gas were helium, for this gas does not condense in contact with liquid nitrogen and would create an overpressure in this closure position of the outlet valve 17. The heating is stopped when it is thought that the pyrolysis is finished (after 5 minutes, for example) and valve 17 is opened so as to let the residual argon escape.

Then trap 7 is removed from the oven by unscrewing, while leaving it in container 18 so that it warms up again slowly while gradually releasing the argon which it contains (valve 17 open).

At the end, only the liquid and solid products of the pyrolysis remain in trap 7 ($C_6+$ in the case of hydrocarbons).

Then a solvent is introduced into trap 7, such as pentane, and a certain amount of the solution obtained is taken with a syringe and is injected into a gas phase chromatography analysis apparatus.

Chloroform may also be introduced into trap 7 and the solution obtained weighed in an aluminium nacelle before effecting liquid phase chromatography, with a view to fractionating the pyrolysis effluents.

In the case where the pyrolysis products are hydrocarbons, this liquid phase chromatography may allow the pyrolysis products to be separated into three families: saturated hydrocarbons, aromatic hydrocarbons, heavy and polar products.

Then a fine analysis of the products of each of these families may be made by gas phase chromatography or mass spectrometry.

What is claimed is:

1. In a device useful for heating of solid or liquid samples taken in small amounts, comprising a tubular liner inside which is defined a zone for heating a sample, heating means located near said zone for heating a sample and means for measuring the temperature in said zone, a sample holder adapted to be introduced into said tubular liner as far as said heating zone, said tubular liner having an effluent outlet orifice which is connected to means enabling measuring and analysis, said device also comprising an orifice for introducing a vector gas for driving along effluents through said heating zone, said orifices being situated on each side of said heating zone, said sample holder comprising a rod which is engaged in said tubular liner and so arranged that there exists a reduced annular space between said rod and said liner for the flow of the vector gas, said rod having an elongate cavity in a side wall of the rod opening into said annular space and adapted for receiving a sample, and means for sealing and positioning said cavity in said tubular liner fitted to said rod at one end of said tubular liner.

2. The device as claimed in claim 1, wherein said tubular liner and said sample holding rod are disposed in a substantially horizontal direction, said cavity being arranged to open upwardly.

3. The device as claimed in claim 1, wherein said sealing and positioning means comprise a compressible ring in which said rod slides, said ring cooperating with a closure member which is threaded, at said one end of said tubular liner, ensuring simultaneously by compression of said ring a seal between said rod and said liner and immobilization of the sample in a predetermined position inside said tubular liner.

4. The device as claimed in claim 1, wherein said tubular liner has a portion that also defines a moderate temperature zone and said rod is movable between a first position in which said cavity containing a sample is situated in the moderate temperature zone of said tubular liner and a second position, in which said cavity is situated in said heating zone.

5. The device as claimed in claim 4, wherein cooling means, comprising a heat radiator is disposed adjacent to said moderate temperature zone of said tubular liner.

6. The device as claimed in claim 1, wherein said tubular liner has a bore with an internal wall made from gold and said rod is also made from gold.

7. The device as claimed in claim 1, wherein said rod comprises means for locating the position of said cavity along and about the axis of said tubular liner when said rod is engaged in said liner.

8. The device as claimed in claim 7, wherein said location means comprises a flat portion formed on said rod, the position of this flat portion being determined so that it remains outside said liner when the rod is engaged in said liner and said cavity positioned in said heating zone, the length of the rod being such that in this position an end engaged in said tubular liner substantially reaches said effluent outlet orifice.

9. The device as claimed in claim 7, wherein a handling member, is fitted to the end of said rod opposite the one end engaged in said tubular liner, said handling member being adapted for limiting the engagement of this rod in said liner by coming into abutment against a closure member.

* * * * *